United States Patent
Sako et al.

(10) Patent No.: US 11,464,416 B2
(45) Date of Patent: Oct. 11, 2022

(54) MEASUREMENT CIRCUIT, DRIVING METHOD, AND ELECTRONIC INSTRUMENT

(71) Applicant: SONY CORPORATION, Tokyo (JP)

(72) Inventors: Michiya Sako, Kagoshima (JP); Masatoshi Kitada, Kagoshima (JP)

(73) Assignee: SONY CORPORATION, Tokyo (JP)

( * ) Notice: Subject to any disclaimer, the term of this patent is extended or adjusted under 35 U.S.C. 154(b) by 309 days.

(21) Appl. No.: 16/083,323

(22) PCT Filed: Mar. 3, 2017

(86) PCT No.: PCT/JP2017/008432
§ 371 (c)(1),
(2) Date: Sep. 7, 2018

(87) PCT Pub. No.: WO2017/159396
PCT Pub. Date: Sep. 21, 2017

(65) Prior Publication Data
US 2019/0090767 A1    Mar. 28, 2019

(30) Foreign Application Priority Data
Mar. 17, 2016   (JP) .............................. JP2016-053645

(51) Int. Cl.
*A61B 5/024*     (2006.01)
*A61B 5/026*     (2006.01)
(Continued)

(52) U.S. Cl.
CPC ........ *A61B 5/02444* (2013.01); *A61B 5/0261* (2013.01); *A61B 5/02416* (2013.01);
(Continued)

(58) Field of Classification Search
CPC ............ A61B 5/02444; A61B 5/02416; A61B 5/6826; A61B 5/7242; A61B 5/1455;
(Continued)

(56) References Cited

U.S. PATENT DOCUMENTS 4,714,341 A   12/1987   Hamaguri et al.
7,714,268 B2   5/2010   Leijssen et al.
(Continued)

FOREIGN PATENT DOCUMENTS

EP    1927002 A2    6/2008
JP    60-176624 A   9/1985
(Continued)

OTHER PUBLICATIONS

International Search Report and Written Opinion of PCT Application No. PCT/JP2017/008432, dated May 30, 2017, 05 pages of English Translation and 06 pages of ISRWO.
(Continued)

*Primary Examiner* — Joseph M Santos Rodriguez
*Assistant Examiner* — Kaitlyn E Sebastian
(74) *Attorney, Agent, or Firm* — Chip Law Group

(57) ABSTRACT

The present technology relates to a measurement circuit, a driving method, and an electronic instrument capable of reducing power consumption. In the measurement circuit, irradiation light is emitted from the light emitting unit toward the object, and light from the object is received to measure pulse waves or the like. The measurement circuit includes: a light receiving unit that receives light from an object; an integrating unit that performs integration of a current generated in accordance with the reception of the light by the light receiving unit and generates a voltage according to the amount of reception of the light; and a pulse generating unit that generates a pulse signal having a pulse width corresponding to the amount of reception of the light
(Continued)

on the basis of the voltage. The present technology can be applied to electronic instruments such as wearable devices, for example.

10 Claims, 7 Drawing Sheets

(51) Int. Cl.
| | |
|---|---|
| *G01J 1/46* | (2006.01) |
| *A61B 5/00* | (2006.01) |
| *A61B 5/1455* | (2006.01) |
| *G01J 1/44* | (2006.01) |
| *G01J 1/42* | (2006.01) |

(52) U.S. Cl.
CPC .......... *A61B 5/1455* (2013.01); *A61B 5/6826* (2013.01); *A61B 5/7225* (2013.01); *A61B 5/7242* (2013.01); *G01J 1/44* (2013.01); *G01J 1/46* (2013.01); *A61B 2560/0209* (2013.01); *G01J 2001/4238* (2013.01); *G01J 2001/446* (2013.01)

(58) Field of Classification Search
CPC ................ A61B 5/7225; A61B 5/0261; A61B 2560/0209; G01J 1/44; G01J 1/46; G01J 2001/4238; G01J 2001/446; G01J 3/18; G01J 3/42; H03M 1/54
See application file for complete search history.

(56) References Cited

U.S. PATENT DOCUMENTS

| | | | | |
|---|---|---|---|---|
| 2009/0026350 | A1* | 1/2009 | Leijssen | A61B 5/0091 250/206 |
| 2013/0077806 | A1* | 3/2013 | Zhang | H03F 1/0233 381/120 |
| 2013/0204143 | A1* | 8/2013 | Narusawa | A61B 5/7214 600/479 |
| 2013/0333477 | A1* | 12/2013 | Kataoka | H02N 2/142 73/655 |
| 2015/0219493 | A1* | 8/2015 | Bungo | G01J 3/18 356/319 |
| 2016/0081602 | A1* | 3/2016 | Lisogurki | A61B 5/0261 600/476 |
| 2016/0089063 | A1* | 3/2016 | Nishida | A61B 5/681 600/316 |
| 2016/0270708 | A1* | 9/2016 | Tateda | A61B 5/742 |

FOREIGN PATENT DOCUMENTS

| | | |
|---|---|---|
| JP | 2009-508102 A | 2/2009 |
| JP | 2012-019926 A | 2/2012 |
| JP | 2013-104839 A | 5/2013 |
| JP | 5572315 B2 | 8/2014 |
| WO | 2007/029191 A2 | 3/2007 |

OTHER PUBLICATIONS

International Preliminary Report on Patentability of PCT Application No. PCT/JP2017/008432, dated Sep. 27, 2018, 06 pages of English Translation and 04 pages of IPRP.

* cited by examiner

MEASUREMENT CIRCUIT, DRIVING METHOD, AND ELECTRONIC INSTRUMENT

CROSS REFERENCE TO RELATED APPLICATIONS

This application is a U.S. National Phase of International Patent Application No. PCT/JP2017/008432 filed on Mar. 3, 2017, which claims priority benefit of Japanese Patent Application No. JP 2016-053645 filed in the Japan Patent Office on Mar. 17, 2016. Each of the above-referenced applications is hereby incorporated herein by reference in its entirety.

TECHNICAL FIELD

The present technology relates to a measurement circuit, a driving method, and an electronic instrument, and particularly relates to a measurement circuit, a driving method, and an electronic instrument capable of reducing power consumption.

BACKGROUND ART

As illustrated in FIG. 1, there is a conventional sensing method that emits light from a light emitting diode (LED) to a site of a human body such as a finger and receives light scattered (reflected) inside the human body by a photodiode (PD) to perform pulse wave measurement and body motion detection.

In an example illustrated in FIG. 1, an LED driver 11 controls to allow an LED 12 to emit light, and then, irradiation light from the LED 12 is emitted to a human finger. Subsequently, the irradiation light is reflected by a blood vessel BV11 inside the finger, and then, the reflected light is received by a sensor 13 formed with a PD.

Since the artery is pulsating in the human body, an absorption rate of the irradiation light emitted from the LED 12 demonstrates a relative change with time in the sampling at several tens of Hz or more and is detected as a pulse wave.

For example, as illustrated in FIG. 2, the sensor 13 obtains an output signal corresponding to the amount of reception of the reflected light at each of times as a result of pulse wave detection. Note that, in FIG. 2, the horizontal axis illustrates time (second) and the vertical axis illustrates the output signal level.

In the example illustrated in FIG. 2, the value of the output signal varies in a cycle with time, and the cycle of this output signal forms the pulse.

As a pulse wave sensing technology like this, there is a proposed technology of allowing the LED to emit light to apply irradiation light to the human body and receiving the reflected light with the PD, and then converting a current generated in the PD into a voltage so as to perform pulse wave sensing (refer to Patent Document 1, for example).

In the technology described in Patent Document 1, four LEDs are provided, and control is performed to allow each of the LEDs to emit light sequentially. In addition, the photoelectric current obtained by receiving the reflected light by the PD is converted into a voltage signal by a resistor connected to the PD, and the voltage signal is further amplified by two amplifiers connected at subsequent stages.

CITATION LIST

Patent Document

Patent Document 1: Japanese Patent Application Laid-Open No. 2012-19926

SUMMARY OF THE INVENTION

Problems to be Solved by the Invention

Meanwhile, lighting time of each of the four LEDs is 0.1 ms to 1 ms according to the technique described in Patent Document 1, and thus, when the sampling rate in detecting a pulse wave is 200 Hz (5 ms), the duty consumed by the LED is 8% to 80%, increasing the power consumption by the LED. That is, the LED emits light for a maximum of 4 ms among the 5 ms period for obtaining one sample of data. In addition, the two amplifiers in the subsequent stage are also operating during the period of voltage conversion with the resistor connected to the PD, leading to power consumption there as well.

Accordingly, in a case where a measurement circuit that measures a pulse wave or the like according to the technology described in Patent Document 1 is mounted with battery drive on a wearable device, for example, the operation time of the wearable device is reduced due to the above-described increase in power consumption, leading to degradation of the commodity value.

The present technology has been made in view of such a situation and aims to be able to reduce power consumption.

Solutions to Problems

A measurement circuit according to a first aspect of the present technology includes: a light receiving unit that receives light from an object; an integrating unit that performs integration of a current generated in accordance with the reception of light by the light receiving unit and generates a voltage according to the amount of reception of the light; and a pulse generating unit that generates a pulse signal having a pulse width corresponding to the amount of reception of the light on the basis of the voltage.

The measurement circuit may further include a light emitting unit that emits light toward the object, and the light receiving unit may be allowed to receive the light emitted to the object by the light emitting unit and reflected by the object.

It is possible to allow the integrating unit to perform integration of the current in any period during a light emission period in which the light is emitted by the light emitting unit, and possible to allow the pulse generating unit to generate the pulse signal after the light emission period.

The measurement circuit may further include a counter that generates digital measurement data corresponding to the amount of reception of the light by measuring the number of clocks input during the pulse width period of the pulse signal.

The integrating unit can be allowed to integrate the current by accumulating electric charges in a capacitor in accordance with the generation of the current.

The integrating unit may include an amplifier on which the capacitor is connected between an inverting input terminal and an output terminal and that outputs the voltage corresponding to the electric charges accumulated in the capacitor.

The integrating unit may include a transistor in which the capacitor is connected to a gate and that generates the voltage corresponding to the electric charges accumulated in the capacitor.

The pulse generating unit may include: a ramp waveform generating unit that generates a ramp wave having a voltage changing in a slope shape on the basis of the voltage obtained by the integrating unit; and a comparator that compares a predetermined voltage with the ramp wave and outputs a comparison result as the pulse signal.

The pulse generating unit may include: a ramp waveform generating unit that generates a ramp wave having a voltage changing in a slope shape; and a comparator that compares the voltage obtained by the integrating unit with the ramp wave and outputs a comparison result as the pulse signal.

A driving method according to a first aspect of the present technology is a method of driving a measurement circuit including: a light receiving unit that receives light from an object; an integrating unit that integrates a current generated in accordance with the reception of the light by the light receiving unit and that generates a voltage in accordance with the amount of received light; and a pulse generating unit that generates a pulse signal having a pulse width corresponding to the amount of reception of the light on the basis of the voltage, the method including generating the voltage by the integrating unit and generating the pulse signal by the pulse generating unit.

According to the first aspect of the present technology, the measurement circuit includes: a light receiving unit that receives light from an object; an integrating unit that performs integration of a current generated in accordance with the reception of light by the light receiving unit and generates a voltage according to the amount of reception of the light; and a pulse generating unit that generates a pulse signal having a pulse width corresponding to the amount of reception of the light on the basis of the voltage.

A electronic instrument according to a second aspect of the present technology includes: a light receiving unit that receives light from an object; and an integrating unit that performs integration of a current generated in accordance with the reception of the light by the light receiving unit and generates a voltage according to the amount of reception of the light; and a pulse generating unit that generates a pulse signal having a pulse width corresponding to the amount of reception of the light on the basis of the voltage.

According to the second aspect of the present technology, the electronic instrument includes: a light receiving unit that receives light from an object; an integrating unit that performs integration of a current generated in accordance with the reception of the light by the light receiving unit and generates a voltage according to the amount of reception of the light; and a pulse generating unit that generates a pulse signal having a pulse width corresponding to the amount of reception of the light on the basis of the voltage.

Effects of the Invention

According to the first and second aspects of the present technology, it is possible to reduce power consumption.

MODE FOR CARRYING OUT THE INVENTION

Hereinafter, embodiments of the present technology will be described with reference to the drawings.

First Embodiment

<Exemplary Configuration of Pulse Wave Sensor System>

Figure 1:
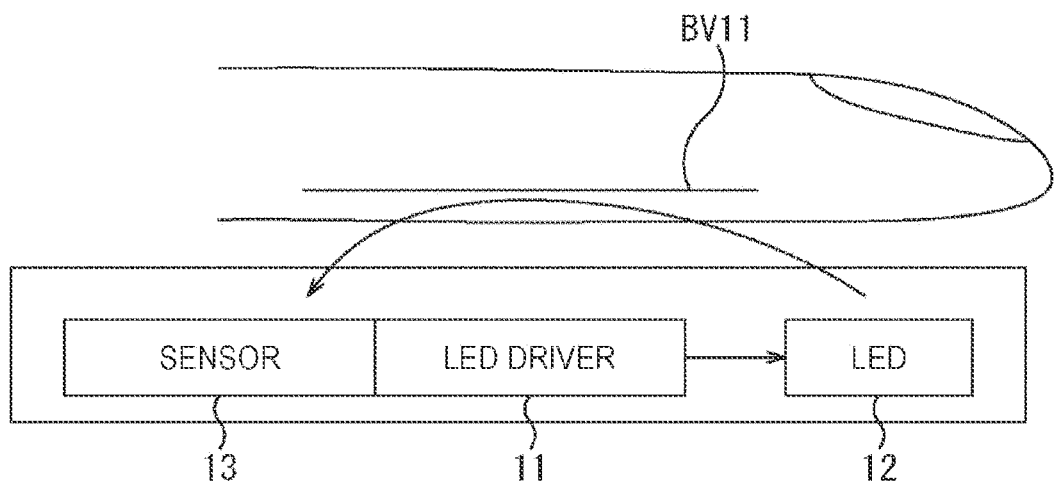
FIG. 1 is a diagram illustrating a general pulse wave measurement.
Figure 2:
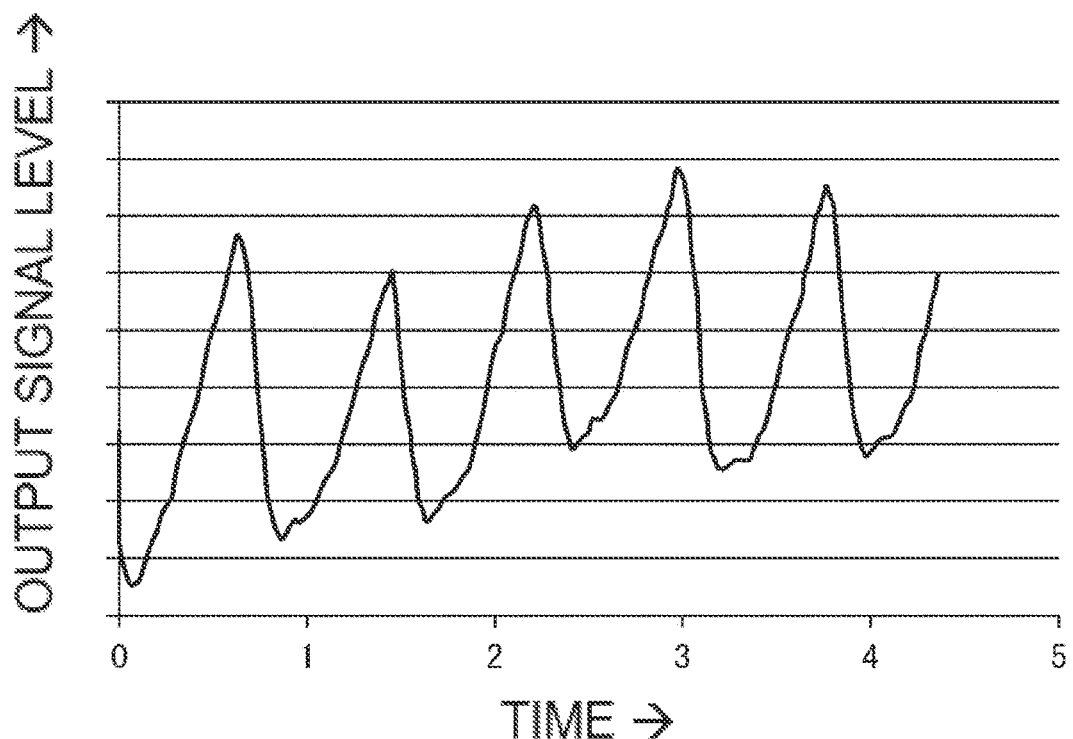
FIG. 2 is a diagram illustrating detection of a pulse wave.
Figure 3:
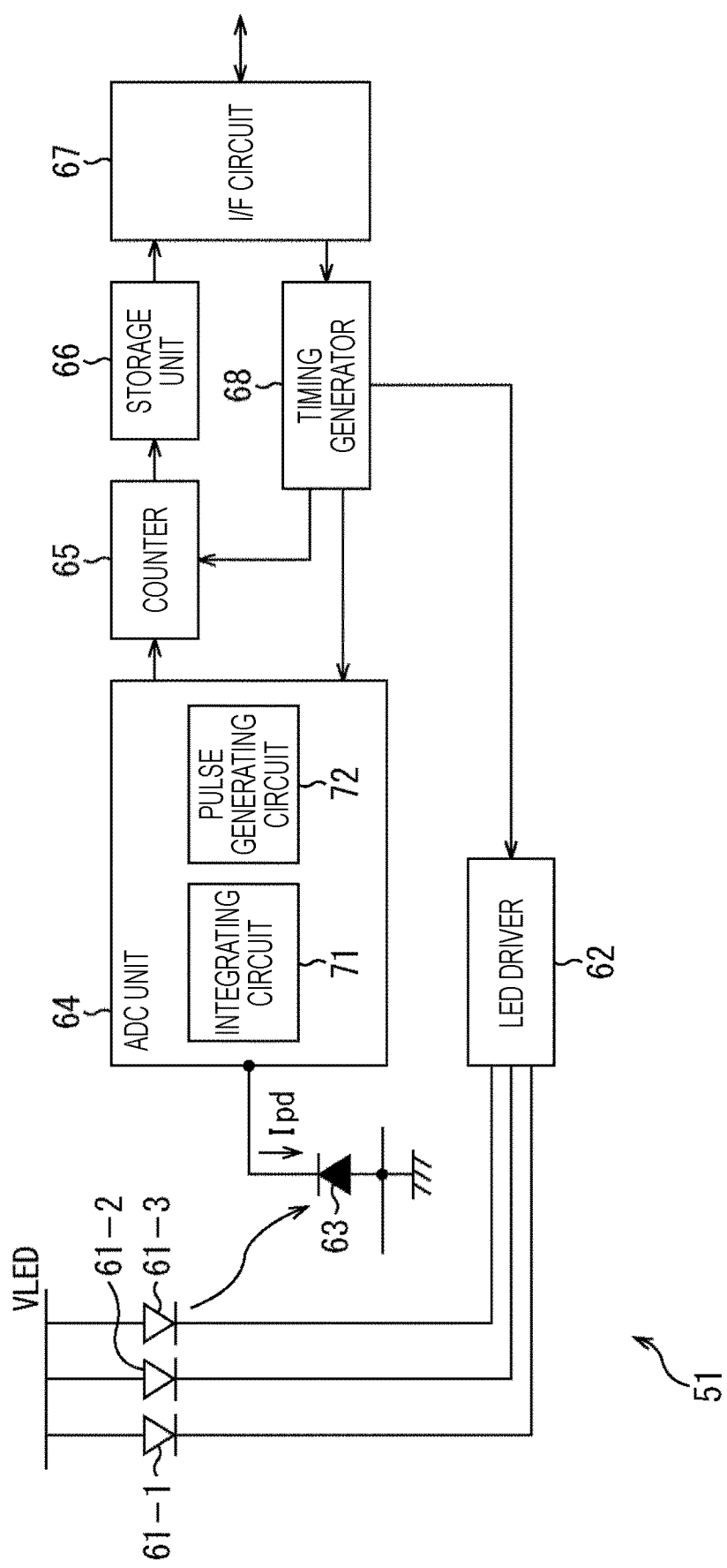
FIG. 3 is a diagram illustrating an exemplary configuration of a pulse wave sensor system.

FIG. 3 is a diagram illustrating a pulse wave sensor system according to an embodiment of the present technology.

A pulse wave sensor system 51 illustrated in FIG. 3 includes a measurement circuit that is an integrated circuit capable of emitting irradiation light to a human body, that is, a wrist, a finger, or the like, and receiving reflected light (scattered light) of the irradiation light to perform pulse wave measurement, body motion detection, or the like. The pulse wave sensor system 51 may be such a measurement circuit itself, or may be various electronic instruments such as a wearable device on which a measurement circuit is mounted. In addition, a measurement target (object) such as the pulse wave is not limited to the human body and may be another living body such as an animal.

The pulse wave sensor system 51 includes LEDs 61-1 to 61-3, an LED driver 62, a PD 63, an analog digital converter (ADC) unit 64, a counter 65, a storage unit 66, an interface (I/F) circuit 67, and a timing generator 68. Note that, in the following description, the LEDs 61-1 to 61-3 will also be referred to simply as the LEDs 61 in a case where there is no need to distinguish between them.

The I/F circuit 67 exchanges signals with the outside. For example, when a control signal is supplied from the outside, the I/F circuit 67 activates the timing generator 68 that determines an operation sequence of individual blocks of the pulse wave sensor system 51. The timing generator 68 generates a clock signal and supplies it to the LED driver 62, the ADC unit 64, and the counter 65.

The LED driver 62 operates the LEDs 61-1 to 61-3 on the basis of the clock signal from the timing generator 68.

Specifically, the LED driver 62 includes a driver circuit for driving the LEDs 61 for each of the LEDs 61, and the LED 61 is connected to each of these driver circuits. Each of the driver circuits constituting the LED driver 62 supplies a current to the LED 61 in connection to allow the LED 61 to emit light.

The LEDs 61-1 to 61-3 are light emitting units that emit light in accordance with the control of the LED driver 62, and emit irradiation light to the human body by light emission.

In this example, each of the LEDs 61-1 to 61-3 outputs irradiation light of mutually different wavelength predetermined for each of applications, toward the human body. Specifically, for example, the irradiation light output from each of the LEDs 61 is light in the wavelength band of each of colors such as red, blue and yellow. The red irradiation light is used in body motion detection, while blue irradiation light is used in pulse measurement. In addition, results of the body motion detection are used for correction according to the body motion of a user wearing a wearable device or the like, for example, in the wearable device or the like including the pulse wave sensor system 51, that is, used for various types of correction corresponding to body motions.

When the irradiation light is output from the LED 61 toward the human body, the irradiation light is reflected inside the human body or the like, and the light generated by reflection (reflected light) is received by the PD 63. The PD 63 is a photodiode that functions as a light receiving unit that receives reflected light from the human body. With reception of the reflected light on the PD 63, the PD 63 generates a current Ipd being a photoelectric current of a magnitude proportional to the amount of reception of the reflected light.

The ADC unit 64 operates on the basis of the clock signal supplied from the timing generator 68. Specifically, the ADC unit 64 converts the current Ipd generated in the PD 63 from a current signal to a voltage signal. In addition, on the basis of the voltage $\Delta V1$ obtained by the current-voltage conversion, the ADC unit 64 generates a pulse signal having a pulse width proportional to the voltage $\Delta V1$, and supplies the pulse signal to the counter 65.

The ADC unit 64 includes: an integrating circuit 71 that integrates the current Ipd to convert the current Ipd into the voltage $\Delta V1$; and a pulse generating circuit 72 that generates a pulse signal having a pulse width proportional to the voltage $\Delta V1$ on the basis of the voltage $\Delta V1$ obtained by the integrating circuit 71.

The counter 65 performs counting operation on the pulse signal output from the pulse generating circuit 72 of the ADC unit 64 on the basis of the clock signal from the timing generator 68 so as to derive a time proportional to the voltage $\Delta V1$.

That is, the counter 65 measures (counts) the number of times of rise or fall of a predetermined reference clock during the pulse width period of the pulse signal, and outputs a measurement result to the storage unit 66. In other words, the counter 65 measures the number of clocks of the reference clock input during the pulse width period of the pulse signal.

The measurement result obtained by the counter 65 is digital data having a value proportional to the total amount of reception of the reflected light received by the PD 63. Accordingly, with the operation of the ADC unit 64 and the counter 65, the reflected light received by the PD 63 is analog-to-digital (AD) converted to digital data indicating the amount of reception of the reflected light. Hereinafter, the data indicating the measurement result output from the counter 65 will also be referred to as measurement data.

The storage unit 66 is formed with a register that holds measured data or the like, for example, and captures the measurement data output from the counter 65, then stores it in an internal register, while outputting the measurement data stored in the register to the I/F circuit 67. The I/F circuit 67 reads the measurement data from the storage unit 66 at a predetermined timing, and outputs the measurement data to the outside as a measurement result of a pulse wave or the like.

<Operation Sequence of Pulse Wave Sensor System>

Next, an operation sequence of the pulse wave sensor system 51 will be described.

Figure 4:
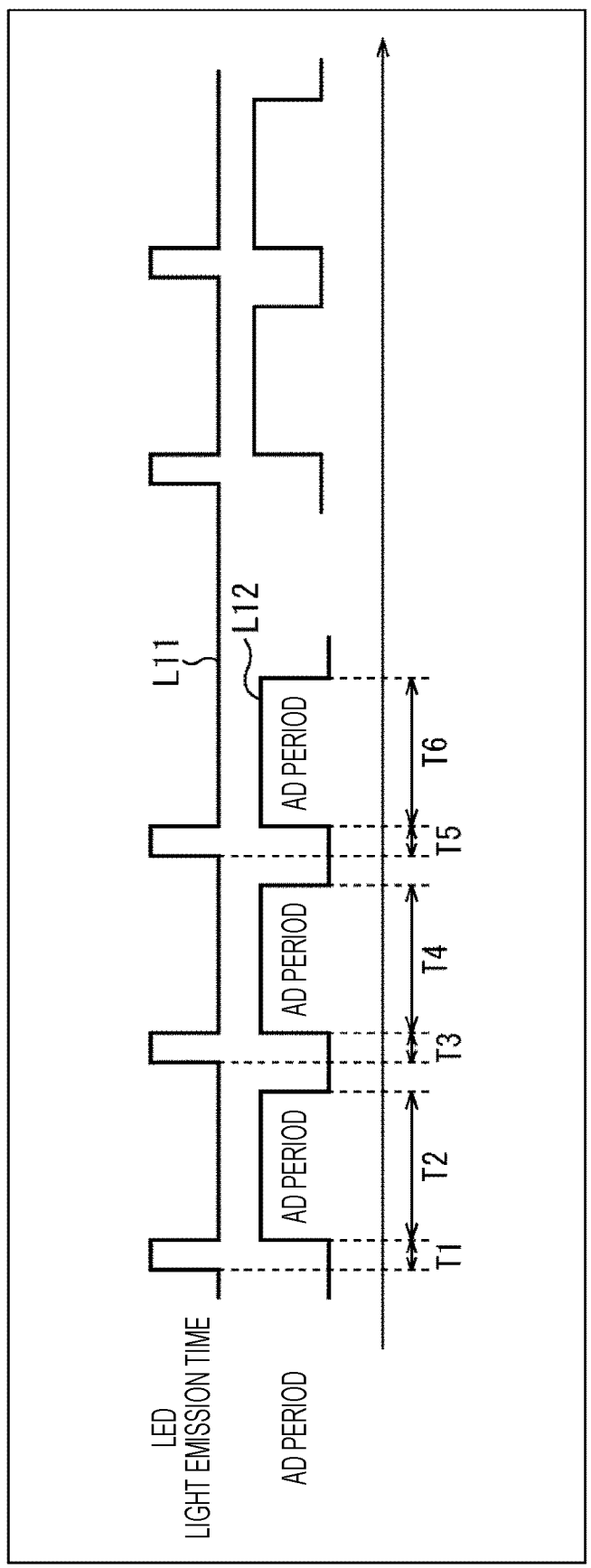
FIG. 4 is a diagram illustrating an operation sequence of the pulse wave sensor system.

As illustrated in FIG. 4, the pulse wave sensor system 51 allows each of the LEDs 61 to emit light in order to perform measurement, for example. Note that, in FIG. 4, the lateral direction indicates time, a polygonal line L11 indicates light emission time of the LED 61, and a polygonal line L12 indicates a period during which AD conversion is performed. In other words, a period during which the polygonal line L11 protrudes upward in the figure indicates a light emission period of the LED 61. In addition, a period during which the polygonal line L12 protrudes upward indicates a period of execution of AD conversion to measurement data.

The pulse wave sensor system 51 performs operation of allowing the LED 61 to emit light for a short time and thereafter performs AD conversion to obtain measurement data.

That is, the LED driver 62 allows the LED 61-1 alone to emit light in a first period T1, for example. At this time, the integrating circuit 71 of the ADC unit 64 integrates the current Ipd generated in accordance with the reception of the reflected light to generate the voltage $\Delta V1$.

Subsequently, the light emission of the LED 61-1 is stopped during a period T2 following the period T1, while the ADC unit 64 and the counter 65 perform AD conversion of the voltage $\Delta V1$ obtained in accordance with the light emission by the LED 61-1 into measurement data.

Following the acquisition of the measurement data corresponding to the LED 61-1 in this manner, the LED driver 62 similarly allows the LED 61-2 alone to emit light during a period T3, and the integrating circuit 71 of the ADC unit 64 similarly integrates the current Ipd to obtain the voltage $\Delta V1$. Moreover, the light emission of the LED 61-2 is stopped during a period T4 following the period T3, while the ADC unit 64 and the counter 65 perform AD conversion of the voltage $\Delta V1$ obtained in accordance with the light emission by the LED 61-2 into measurement data.

Furthermore, the LED driver 62 allows the LED 61-3 alone to emit light during a period T5, and the integrating circuit 71 of the ADC unit 64 integrates the current Ipd to obtain the voltage $\Delta V1$. Moreover, the light emission of the LED 61-3 is stopped during a period T6 following the period T5, while the ADC unit 64 and the counter 65 perform AD conversion of the voltage $\Delta V1$ obtained in accordance with the light emission by the LED 61-3 into measurement data.

Now, measurement data for one sample has been obtained for each of applications such as pulse wave measurement by the above operation from the period T1 to the period T6. That is, one sample period has been finished. Thereafter, the above-described operation is repeatedly performed to continuously measure the pulse wave or the like.

In this manner, with an integral type AD conversion mechanism that integrates the current Ipd during the light emission period of the LED 61 and converts the voltage $\Delta V1$ being the integration result of the current Ipd into the measurement data after the light emission period, it is possible to reduce the light emission time of the LED 61 to the time as short as about a several hundredth of the sampling rate with the emission cycle of the LED 61 being similar to the conventional case. This makes it possible to reduce consumption current needed to drive the LED 61, that is, reduce power consumption. In addition, with such a configuration, it is possible to stably obtain biological information such as a pulse wave with high accuracy.

<Exemplary Configuration of ADC Unit>

Now, a more specific configuration example of the ADC unit 64 provided in the pulse wave sensor system 51 will be described.

Figure 5:
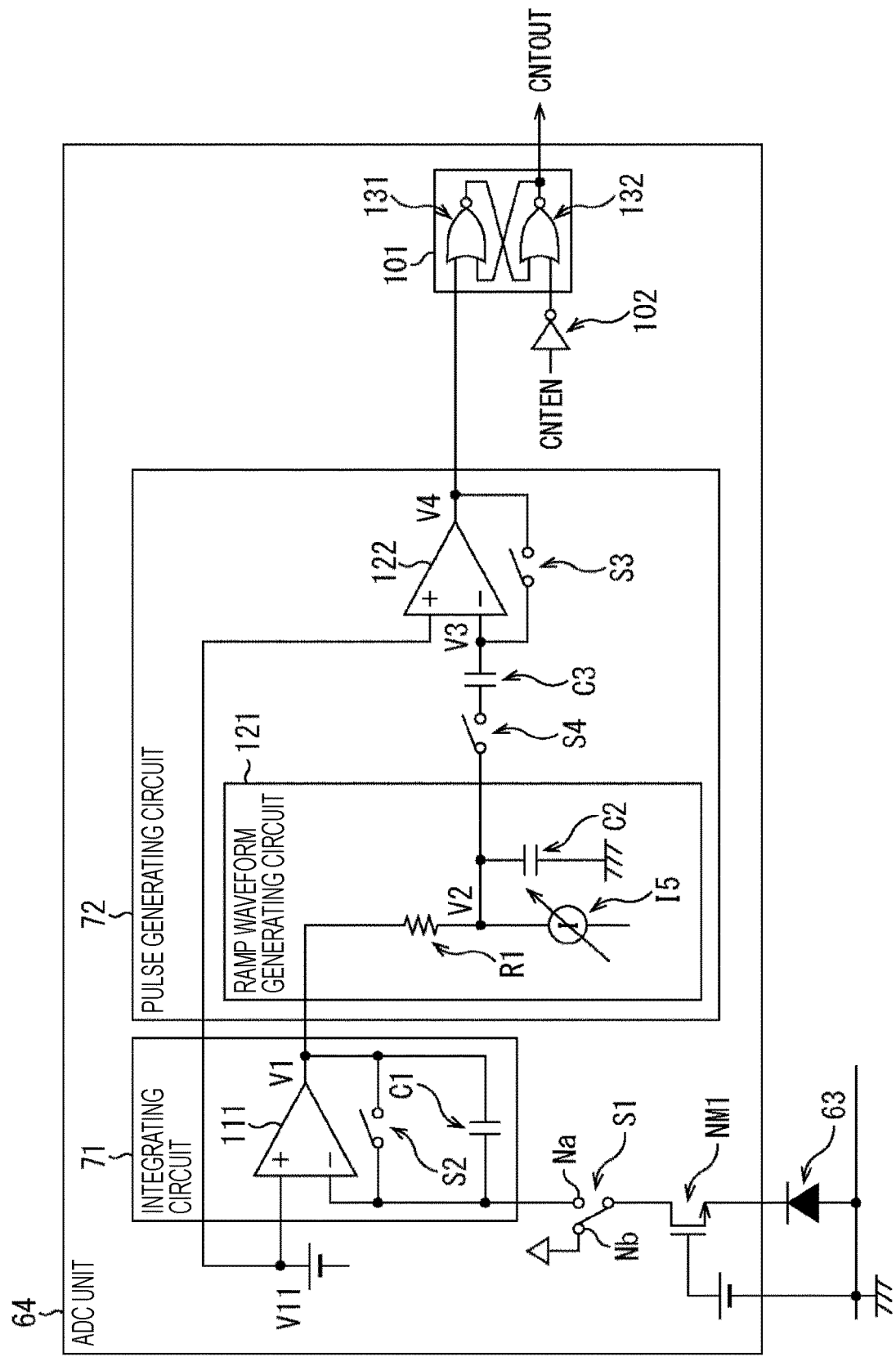
FIG. 5 is a diagram illustrating an exemplary configuration of an ADC unit.

An example of more specific configuration of the ADC unit 64 is as illustrated in FIG. 5. Note that, in FIG. 5, portions corresponding to those in FIG. 3 are denoted by the same reference numerals, and description thereof is omitted as appropriate.

The ADC unit 64 illustrated in FIG. 5 includes a transistor NM1, a switch S1, the integrating circuit 71, the pulse generating circuit 72, a flip-flop 101, and an inverter 102.

In this example, the PD 63 is connected to the integrating circuit 71 via the transistor NM1 and the switch S1, while the integrating circuit 71 includes an amplifier 111, a switch S2, and the capacitor C1.

That is, in the ADC unit 64, the PD 63 that generates the current Ipd is biased by the transistor NM1, and the switch S1 for storing electric charges in the capacitor C1 for a predetermined integration time is connected to the drain of the transistor NM1. The switch S1 switches the connection destination so as to cause the PD 63 to be connected to either one of a node Na on the integrating circuit 71 side and a node Nb on the ground side.

In the integrating circuit 71, the non-inverting input terminal of the amplifier 111 is connected to the power supply of a predetermined voltage value V11, and the capacitor C1 for integrating the current Ipd and a switch S2 for resetting are connected in parallel between the output terminal and the inverting input terminal of the amplifier 111. In addition, the inverting input terminal of the amplifier 111 is also connected with the node Na. Note that the voltage V11 of the power supply is a predetermined fixed voltage value.

Due to the operation of the amplifier 111, the voltage with a same level as the voltage V11 is constantly generated as an imaginary short-circuit at the inverting input terminal of the amplifier 111. Furthermore, during the integration operation of the integrating circuit 71, the electric charges corresponding to the voltage ΔV1 are accumulated in the capacitor C1. In the following description, the voltage at the output terminal of the amplifier 111 will be referred to as voltage V1.

In addition, the pulse generating circuit 72 provided at a subsequent stage of the integrating circuit 71 includes a ramp waveform generating circuit 121, a switch S4, a capacitor C3, a comparator 122, and a switch S3. Furthermore, the ramp waveform generating circuit 121 has a resistor R1, a constant current source I5, and a capacitor C2.

The output terminal of the amplifier 111 is connected to one end of the resistor R1 constituting the ramp waveform generating circuit 121. The constant current source I5, the capacitor C2, and the switch S4 are connected to the other end of the resistor R1. In the following description, the voltage at the end of the resistor R1 on the switch S4 side will be referred to as voltage V2.

In the ramp waveform generating circuit 121, the voltage V2 after the integration operation by the integrating circuit 71 can be decreased with a constant time constant by the resistor R1, the constant current source I5, and the capacitor C2. That is, the ramp waveform generating circuit 121 generates a ramp wave having a voltage value changing in a slope shape on the basis of the voltage ΔV1.

In addition, an inverting input terminal of the comparator 122 is connected to the end of the switch S4 on the opposite side to the resistor R1 side via the capacitor C3. The pulse generating circuit 72 includes the switch S4 and the capacitor C3 in order to transmit the voltage ΔV1 alone obtained by the integration operation of the integrating circuit 71 to the comparator 122.

The non-inverting input terminal of the comparator 122 is connected to the power supply of a predetermined voltage value V11, with a switch S3 for canceling an offset of the comparator 122 being connected between the inverting input terminal and the output terminal of the comparator 122. In particular, the end on the inverting input terminal side of the comparator 122 in the switch S3 is connected between the inverting input terminal and an electrode on the comparator 122 side of the capacitor C3. In the following description, the voltage between the capacitor C3 and the inverting input terminal of the comparator 122 will also be referred to as voltage V3. In addition, in the following description, the voltage at the output terminal of the comparator 122 will also be referred to as voltage V4.

Furthermore, a flip-flop 101 is connected to the output terminal of the comparator 122. The flip-flop 101 is an RS flip-flop and is formed with a NOR gate 131 and a NOR gate 132.

The output terminal of the comparator 122 is connected to one input terminal of the NOR gate 131, and the output terminal of the NOR gate 132 is connected to the other input terminal of the NOR gate 131. In addition, the output terminal of the NOR gate 131 is connected to one input terminal of the NOR gate 132, and the inverter 102 is connected to the other input terminal of the NOR gate 132. Furthermore, the counter 65 is connected to the output terminal of the NOR gate 132.

As a set of the flip-flops 101, a control signal CNTEN is input to the NOR gate 132 of the flip-flop 101 via the inverter 102. That is, the polarity inverted signal of the control signal CNTEN is input to the NOR gate 132.

On the basis of the voltage V4 being an output of the comparator 122, the flip-flop 101 generates a pulse signal having a pulse width proportional to the voltage ΔV1 and outputs the generated pulse signal to the counter 65. Hereinafter, the pulse signal output from the flip-flop 101 will also be referred to as a pulse signal CNTOUT.

<Operation of ADC Unit>

Next, operation of the ADC unit 64 will be described with reference to a timing chart of FIG. 6. Note that, in FIG. 6, the lateral direction indicates time. In addition, in FIG. 6, polygonal lines L21 to L32 respectively represent turn on/off of the LED 61, a connection state of the switch S1, a connection state of the switch S2, a connection state of the switch S3, a connection state of the switch S4, the voltage V1, a current flowing through the constant current source I5, the voltage V2, the voltage V3, the voltage V4, the control signal CNTEN, and the pulse signal CNTOUT.

In the polygonal line L21, an upward protrusion state in the figure indicates a state of light emission (turning on) of the LED 61, while downward protrusion state in the figure indicates a state of turning off, namely, a non-light emitting state of the LED 61. Moreover, in the polygonal line L22, an upward protrusion state in the figure indicates a state where the switch S1 is connected to the node Na side, while the downward protrusion state in the figure indicates a state where the switch S1 is connected to the node Nb side.

In the polygonal line L23 to polygonal line L25, the upward protrusion state in the figure respectively indicates a state where the switches S2 to S4 are turned on, while the downward protrusion state in the figure indicates a state where the switches S2 to S4 are respectively turned off. In addition, in the polygonal line L31 and polygonal line L32, the upward protrusion state in the figure indicates a high level of each of the control signal CNTEN and the pulse signal CNTOUT, that is, the state of "1", while the downward protrusion state in the figure indicates a low level of each of the control signal CNTEN and pulse signal CNTOUT, that is, the state of "0".

Figure 6:
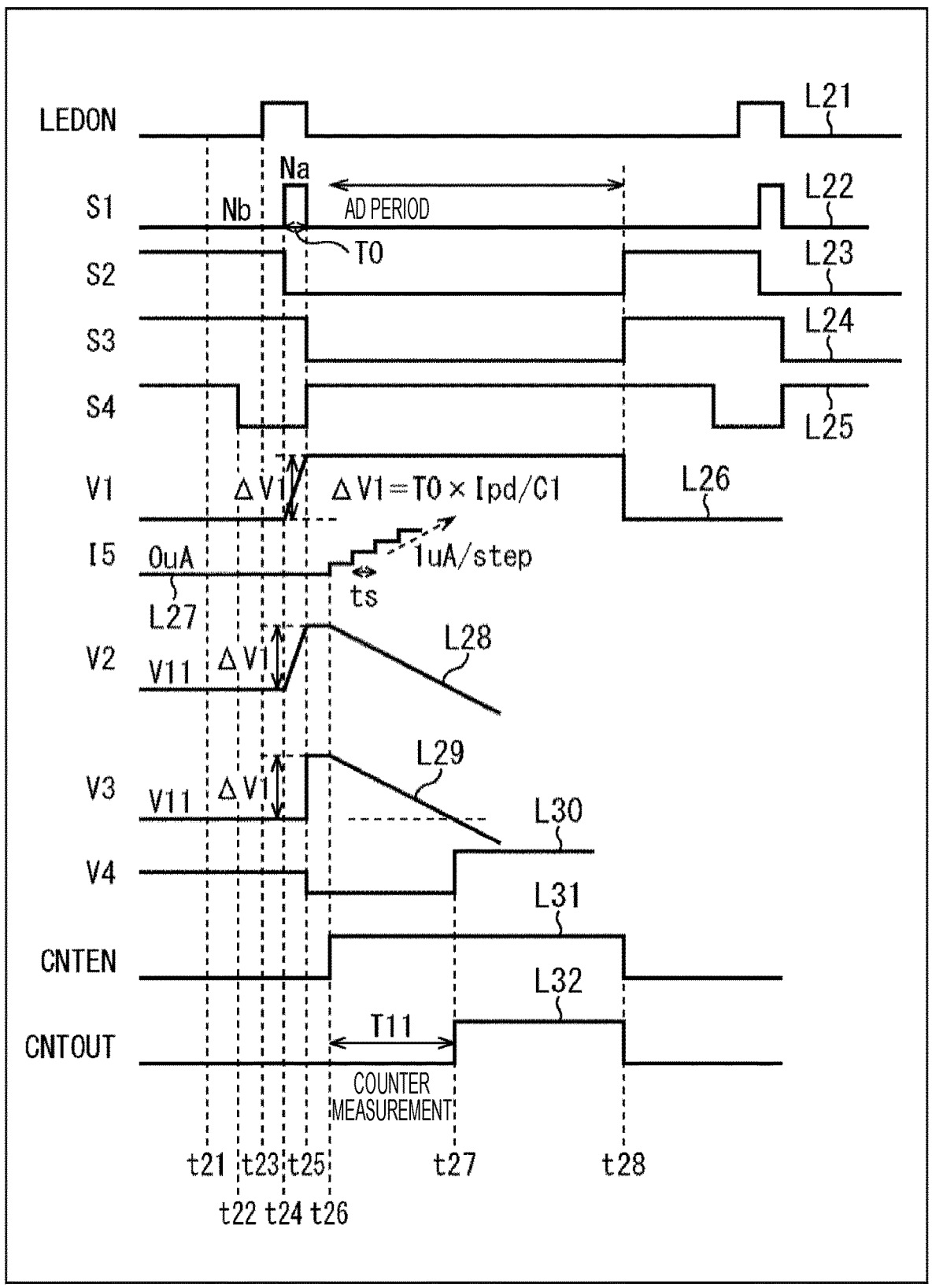
FIG. 6 is a diagram illustrating an operation sequence of the ADC unit.

In the example illustrated in FIG. 6, at time t21 before light emission of the LED 61, the connection destination of the switch S1 is set to the node Nb, and the switches S2 to S4 are set to be turned on. In addition, the control signal CNTEN is set to "0", and the current flowing through the constant current source I5 is set to 0 µA. At this time, the value of the pulse signal CNTOUT is "0".

At time t21, before light emission of the LED 61, operation for canceling the offset of the comparator 122 is performed at both ends of the capacitor C3.

With the switches S2 to S4 turned on, the value of the voltage V2 becomes substantially V11 although the offset of the amplifier 111 is included, with the amplifier 111 as a buffer. That is, substantially the same potential level as the voltage V11 is generated at the end of the resistor R1 opposite to the amplifier 111 side.

In addition, the value of the voltage V3 is also substantially V11 although the offset of the comparator 122 is included. That is, substantially the same potential level as the voltage V11 is generated at the inverting input terminal of the comparator 122. This causes the electric charge corresponding to a difference due to the offset voltage between the amplifier 111 and the comparator 122 to be stored and held in the capacitor C3.

Thereafter, the switch S4 is turned off at time t22, and furthermore, the LED driver 62 causes one LED 61, for example, the LED 61-1 to emit light at time t23. When the LED 61-1 emits light, the PD 63 receives reflected light from the human body, whereby a current Ipd is generated in the PD 63.

At time t24, the ADC unit 64 sets the connection destination of the switch S1 to the node Na, and the integrating circuit 71 turns off the switch S2. This electrically connects the PD 63 and the capacitor C1 via the transistor NM1 and the switch S1, leading to accumulation of electric charges in the capacitor C1 in accordance with the generation of the current Ipd.

That is, electric charges are stored (accumulated) continuously in the capacitor C1 during the period in which the current Ipd flows, and the voltage V1 increases in accordance with an increase in the amount of electric charges accumulated in the capacitor C1. In other words, the amplifier 111 outputs the voltage V1 corresponding to the amount of the electric charges accumulated in the capacitor C1, that is, the voltage $\Delta V1$.

In this manner, during the period in which the switch S1 is connected to the node Na, the integration operation of the current Ipd with respect to the capacitor C1 is performed so as to increase the voltage V1.

At this time, the amount of change in the voltage V1 during the period from the point of start of connection of the switch S1 to the node Na to the state where the storage of the electric charge in the capacitor C1 has been finished, that is, the period until time t25 to be described below is the voltage $\Delta V1$. This voltage $\Delta V1$ is a value proportional to the total amount of reflected light received by the PD 63, that is, the total amount of reception of the reflected light.

At time t25, the LED driver 62 stops light emission of the LED 61, and the ADC unit 64 sets the connection destination of the switch S1 to the node Nb. In addition, the pulse generating circuit 72 turns off the switch S3 and turns on the switch S4.

When the connection destination of the switch S1 is returned from the node Na to the node Nb in this manner, the potential of the output of the amplifier 111, that is, the value of the voltage V1 is held at V11+$\Delta V1$. Moreover, the current flowing through the constant current source I5 is 0 µA at this point, leading to acquisition of the voltage V2 having same value (same potential) as the voltage V1. The above integration operation has integrated the current Ipd so as to obtain the voltage $\Delta V1$.

When the switch S3 is turned off together with the end of the integration operation and the switch S4 is turned on from this state, the value $\Delta V1$ alone among the value V11+$\Delta V1$ of the voltage V2 is transmitted by capacitive coupling of the capacitor C3 to the inverting input terminal of the comparator 122, leading to acquisition of the value of the voltage V3 being substantially V11+$\Delta V1$.

Moreover, after the switch S3 is turned off, the comparator 122 compares the voltage V11 of the non-inverting input terminal with the voltage V3 of the inverting input terminal, and outputs a comparison result as the voltage V4 to the flip-flop 101. At this point, since the voltage V3 of the inverting input terminal is larger than the voltage V11 of the non-inverting input terminal, the voltage V4 is set to the low level, that is, "0". Therefore, in this state, the value of the pulse signal CNTOUT output from the flip-flop 101 is "0".

Note that the period from time t23 to the time 25 as the light emission period of the LED 61 corresponds to the period T1 illustrated in FIG. 4, for example.

Here, the length of the period from time t24 to time t25 during which the connection destination of the switch S1 is set to the node Na, that is, the length of the period during which the integration operation of the current Ipd is performed by the integrating circuit 71 is defined as integration time T0, the magnitude of the current Ipd is defined as Ipd, and the capacitance value of the capacitor C1 is defined as C1. Under this setting, the voltage $\Delta V1$ is $\Delta V1 = T0 \times Ipd/C1$.

In addition, the above has described an example in which the integration operation of the current Ipd is started after the start of the light emission period of the LED 61 and the integration operation is finished together with the end of the light emission period of the LED 61. Alternatively, the period during which the integration operation of the current Ipd is performed can be any period as long as it is during the light emission period of the LED 61.

At time t26, the ADC unit 64 sets the control signal CNTEN to "1" and together with this, the ramp waveform generating circuit 121 controls the constant current source I5 such that the current flowing through the constant current source I5 increases by a fixed amount at every predetermined unit time ts. In this example, control is performed to allow the current flowing through the constant current source I5 to increase by 1 µA at every unit time ts, that is, the current increases stepwise.

Here, the resistance value of the resistor R1 is defined as R1, and the capacitance value of the capacitor C2 is defined as C2. In this case, in a case where the time constant of R1×C2 is sufficiently larger than the unit time ts, the voltage change of the output of the ramp waveform generating circuit 121, that is, the change in the voltage V2 can be obtained as the waveform of slope (ramp waveform) similar to the gradient of the change in the current flowing through the constant current source I5. Since the inverting input terminal side of the comparator 122 is at high impedance, the same voltage waveform as the voltage V2 is obtained as the voltage V3 via the capacitor C3.

In this example, it is observed that the voltage V2 decreases with a constant gradient together with the increase in the current flowing through the constant current source I5 and that this results in a decrease of the voltage V3 similarly to the voltage V2. That is, it can be seen that a voltage signal (ramp wave) of a ramp waveform indicated by the voltage V3 is input to the inverting input terminal of the comparator 122.

The comparator 122 compares the ramp wave input to the inverting input terminal, that is, the voltage V3 with the fixed voltage V11 input to the non-inverting input terminal, and outputs a comparison result as a pulse signal, more specifically as the voltage V4 for obtaining a pulse signal.

In addition, the counter 65 starts counting the reference clock at time t26.

At this point, since the voltage V3 of the inverting input terminal is larger than the voltage V11 of the non-inverting input terminal, the voltage V4 being the output of the comparator 122 is a low level and the value of the pulse signal CNTOUT is also low level, that is, remains at "0".

Thereafter, the voltage V3 gradually decreases. When the voltage V3 of the inverting input terminal becomes equal to the voltage V11 of the non-inverting input terminal at time t27, that is, after the voltage V3 decreases by $\Delta V1$, the voltage V4 being the output of the comparator 122 transitions to the high level. That is, the voltage V4 is inverted from "0" to "1".

This causes the flip-flop 101 to be reset, and the pulse signal CNTOUT output from the flip-flop 101 changes to the high level. That is, the value of the pulse signal CNTOUT is inverted from "0" to "1".

The counter 65 finishes counting of the reference clock at the timing when the value of the pulse signal CNTOUT becomes "1", and outputs the count result to the storage unit 66 as measurement data.

That is, the period T11 from the rising edge of the control signal CNTEN, which is the trigger signal for starting the AD conversion, to the rising edge of the pulse signal CNTOUT corresponds to the voltage $\Delta V1$, that is, the pulse width proportional to the amount of reception of the reflected light by the PD 63. The counter 65 measures the length of the period of the pulse width on the basis of the internal reference clock, so as to convert the pulse width of the pulse signal CNTOUT into a digital quantity and generate measurement data.

Note that while it is also conceivable to convert the current Ipd into an oscillation frequency proportional to the magnitude of the current Ipd to obtain measurement data, it would be difficult, in this case, to ensure the linearity of the oscillation frequency. In contrast, the pulse wave sensor system 51 converts the current Ipd into the voltage, and changes the voltage V3 in a slope shape to measure the time until the pulse signal CNTOUT is inverted. With this measurement, it is possible to stably perform measurement with high accuracy without necessity of considering the linearity in frequency.

Furthermore, after the digital measurement data is obtained, the integrating circuit 71 turns on the switch S2 at time t28, and the pulse generating circuit 72 turns on the switch S3. As a result, the value of the voltage V1 becomes V11. In addition, at time t28, the control signal CNTEN is set to "0", and the value of the pulse signal CNTOUT is "0".

The period from time t25 to time t28 corresponds to the period T2 illustrated in FIG. 4, for example.

Measurement data for one LED 61 has been obtained by the operation so far, and thereafter, the operation for obtaining the measurement data of each of the LEDs 61 including the other LEDs 61 is performed continuously and repeatedly.

As described above, with the pulse wave sensor system 51 including an integral type AD conversion mechanism that integrates the current obtained by receiving the reflected light, converts it into voltage, and further converts the voltage into measurement data, it is possible to reduce the light emission time of the LED 61 to about one several hundredth of the time in conventional cases. This makes it possible to reduce the contribution rate of current consumption needed for driving the LED 61 with respect to the current consumption of the entire pulse wave sensor system 51 to about a several hundredths, leading to suppression of the power consumption of the entire system by a several tenths of the conventional case.

For example, now it is assumed that the sampling rate for sampling the measurement data of one measurement for all three LEDs 61 is 200 Hz, that is, the time needed for one sampling (measurement) is 5 ms. In addition, it is assumed that a current of 30 mA is needed for light emission of one LED 61, the light emitting time of one LED 61 is 5 µs, and the total light emission time for the three LEDs 61 is 15 µs. Furthermore, it is assumed that the time needed for data communication such as transmission of measurement data in one sampling is 2 ms, and that the circuit current needed for operation of the entire pulse wave sensor system 51 (excluding driving of the LED driver 62) in one sampling period is 1 mA.

In such a case, the average current of the pulse wave sensor system 51 is ((30 mA×15 µs)+(1 mA×5 ms))/5 ms=1.09 mA, indicating achievement of low power consumption.

The pulse wave sensor system 51 can greatly reduce power consumption, and thus, for example, it is possible to drive a wearable device for a long time in a case where the pulse wave sensor system 51 is applied to the wearable device such as a smart band, leading to enhancement of the commercial value. In view of expansion of health markets in recent years in particular, implementation of the pulse wave sensor system 51 capable of long-term measurement such as a pulse wave in the form of being mounted on the wearable device would enable more accurate physical condition management. In this respect, the wearable device like this can also be used as a device for prevention of disease.

Note that with assumption of occurrence of changes in the current Ipd, which is a photoelectric current, due to the skin color and hairiness of the subject in the measurement of the pulse wave or the like, it is also possible to allow the integration time T0 described with reference to FIG. 6 to be variable, or possible to configure such that one capacitor C1 be selectable from among a plurality of capacitors C1, externally by software, or the like. With a configuration in which selection of the integration time T0 and the capacitor C1 can be controlled from the outside in this manner, it is possible to easily adjust the signal level without substantially increasing the power consumption. In this case, the ADC unit 64 appropriately controls the connection switching timing of the switch S1 to adjust the integration time T0 in accordance with the external control, or the integrating circuit 71 selects one capacitor C1 among the plurality of capacitors C1 and electrically connects the capacitor C1 to the amplifier 111 in accordance with the external control. In addition, the pulse wave sensor system 51 may be configured to be able to externally adjust the light emission time of the LED 61 and the drive current of the LED 61. For example, with the variable drive current for the LED 61, it is possible to change the light emission amount of the LED 61 to adjust the magnitude of the current Ipd.

Furthermore, it would be necessary in general IC design to increase the width of the aluminum wire as a measure against electromigration of the aluminum wiring due to the large current flowing inside the IC. The pulse wave sensor system 51, however, achieves short driving time of the LED 61, and thus can reduce the necessity of increasing the width of the aluminum wire connected to the LED 61. This makes it possible to reduce the chip size, that is, the size of the pulse wave sensor system 51.

Second Embodiment

<Exemplary Configuration of ADC Unit>

In addition, the ADC unit 64 illustrated in FIG. 3 is not limited to the configuration illustrated in FIG. 5, and may have other configurations. For example, the integrating circuit 71 need not have a configuration of using the amplifier 111 and may be configured to use a transistor constituting a source follower circuit instead of the amplifier 111.

Figure 7:
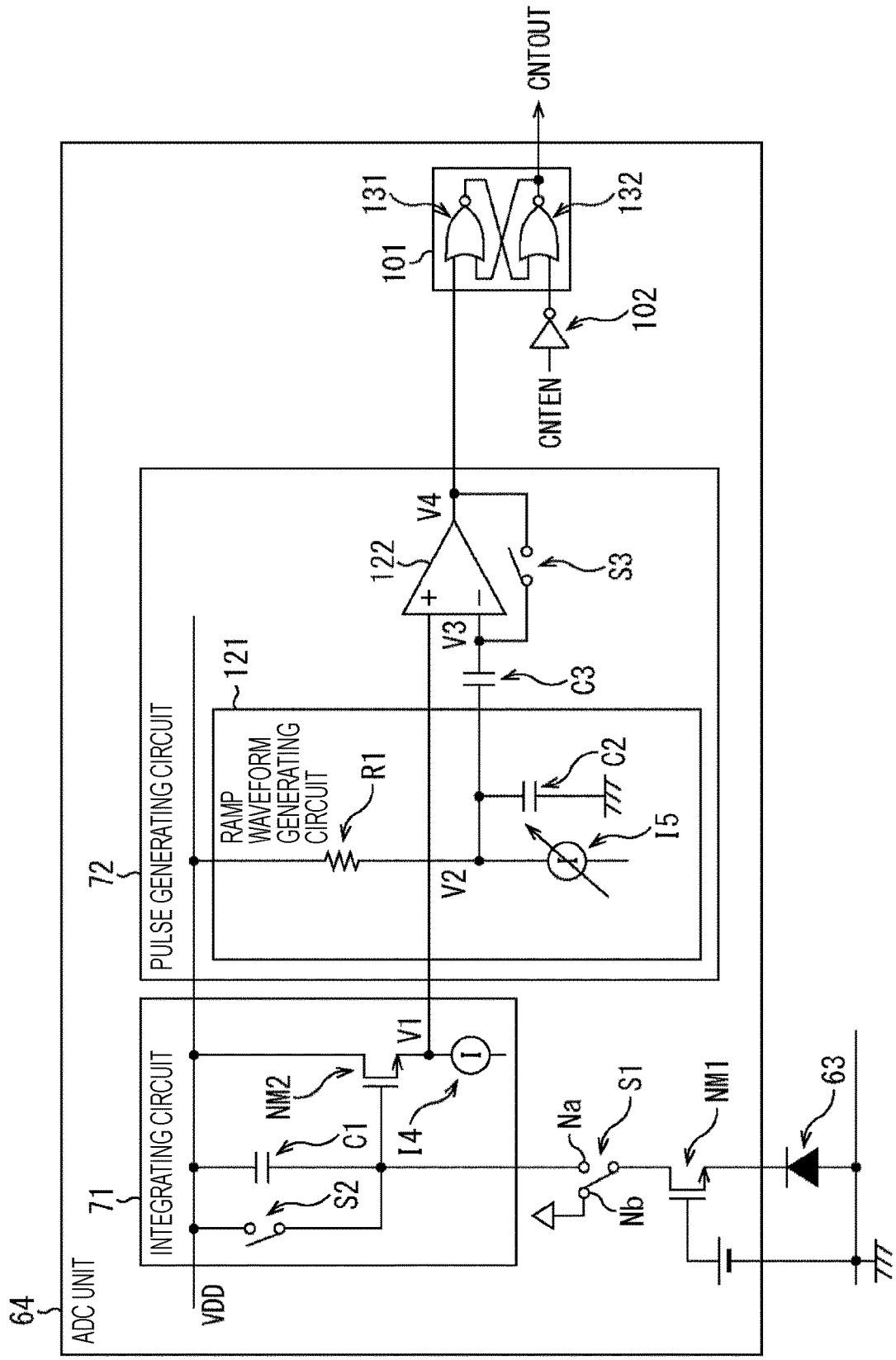
FIG. 7 is a diagram illustrating an exemplary configuration of the ADC unit.

In such a case, the ADC unit 64 is configured as illustrated in FIG. 7, for example. Note that, in FIG. 7, portions corresponding to those in FIG. 5 are denoted by the same reference numerals, and description thereof is omitted as appropriate.

Similarly to the ADC unit 64 illustrated in FIG. 5, the ADC unit 64 illustrated in FIG. 7 includes the transistor NM1, the switch S1, the integrating circuit 71, the pulse generating circuit 72, the flip-flop 101, and the inverter 102, with a connection relationship similarly to the example of FIG. 5. In the ADC unit 64 illustrated in FIG. 7, merely the internal configuration of the integrating circuit 71 and the pulse generating circuit 72 is different from the configuration of the ADC unit 64 illustrated in FIG. 5.

That is, in the example of FIG. 7, the integrating circuit 71 includes the capacitor C1, the switch S2, a constant current source 14, and a transistor NM2.

In the integrating circuit 71, the switch S2 and the capacitor C1 are connected to the node Na. Moreover, an end of the switch S2 on the side opposite to the node Na side and an electrode on the side opposite to the node Na side of the capacitor C1 are connected to a predetermined power supply of the voltage VDD. Here, the power supply voltage VDD is a fixed voltage.

A gate of the transistor NM2 which is an nMOS transistor is also connected to the node Na. Therefore, the integrating circuit 71 has a configuration in which the capacitor C1 for integrating the current Ipd is connected between the power supply of the voltage VDD and the gate of the transistor NM2.

In addition, the drain of the transistor NM2 is connected to the power supply of the voltage VDD, and the source of the transistor NM2 is connected to the constant current source 14. In this embodiment, the voltage on the source side of the transistor NM2 is referred to as voltage V1.

The pulse generating circuit 72 includes the ramp waveform generating circuit 121, the capacitor C3, the comparator 122, and the switch S3. Unlike the example illustrated in FIG. 5, the pulse generating circuit 72 illustrated in FIG. 7 does not include the switch S4 between the ramp waveform generating circuit 121 and the capacitor C3.

The ramp waveform generating circuit 121 includes the resistor R1, the constant current source I5, and the capacitor C2. While the connection relationship between the resistor R1, the constant current source I5, and the capacitor C2 is the same as the example illustrated in FIG. 5, the end of the resistor R1 on the side different from the constant current source I5 side is connected to the power supply of the voltage VDD. In this embodiment, the voltage at the end of the resistor R1 on the constant current source I5 side is also referred to as voltage V2 similarly to the case of the first embodiment.

Moreover, the inverting input terminal of the comparator 122 is connected to the constant current source I5 side end of the resistor R1 via the capacitor C3, while the non-inverting input terminal of the comparator 122 is connected to the source of the transistor NM2 in the integrating circuit 71. Furthermore, a switch S3 is connected between the output terminal and the inverting input terminal of the comparator 122.

In the present embodiment, the voltage between the inverting input terminal of the comparator 122 and the capacitor C3 will also be referred to as the voltage V3 and the voltage of the output terminal of the comparator 122 as the voltage V4, similarly to the case of the first embodiment.

In the ADC unit 64 with this configuration, the operation sequence of the switch S1, the switch S2, and the constant current source I5 is similar to the case of the ADC unit 64 illustrated in FIG. 5, except that the operation sequence of the switch S3 is the same as the sequence of the switch S2.

<Operation of ADC Unit>

Next, operation of the ADC unit 64 illustrated in FIG. 7 will be described with reference to a timing chart of FIG. 8. Note that, in FIG. 8, portions corresponding to those in FIG. 6 are denoted by the same reference numerals, and description thereof is omitted as appropriate.

Figure 8:
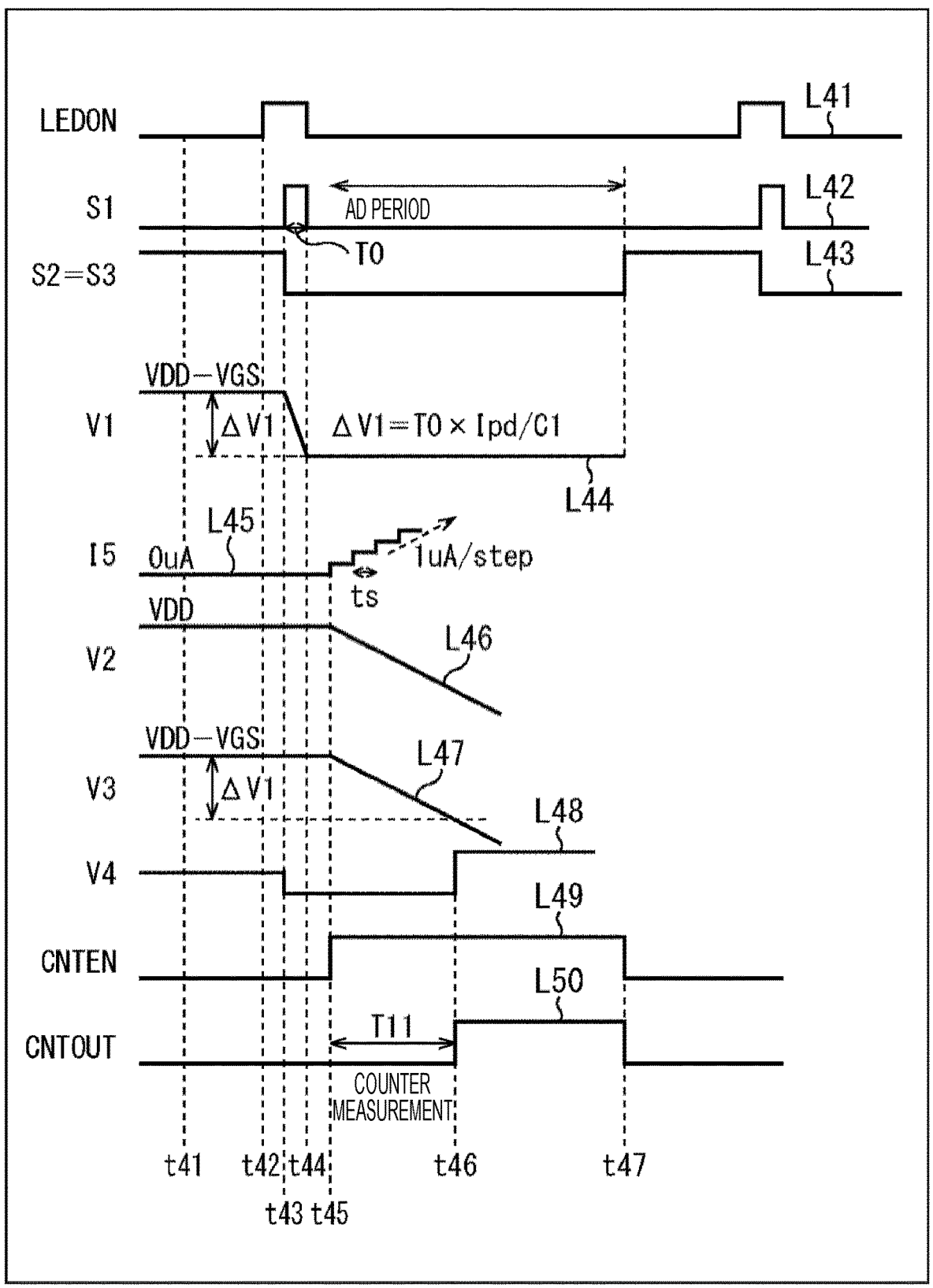
FIG. 8 is a diagram illustrating an operation sequence of the ADC unit.

In FIG. 8, the lateral direction indicates time. In addition, in FIG. 8, polygonal lines L41 to L50 respectively represent turn on/off of the LED 61, a connection state of the switch S1, connection states of the switches S2 and S3, the voltage V1, a current flowing through the constant current source I5, the voltage V2, the voltage V3, the voltage V4, the control signal CNTEN, and the pulse signal CNTOUT.

In the polygonal line L41, the upward protrusion state in the figure indicates a state of light emission (turning on) of the LED 61, while the downward protrusion state in the figure indicates a state of turning off of the LED 61. Moreover, in the polygonal line L42, an upward protrusion state in the figure indicates a state where the switch S1 is connected to the node Na side, while the downward protruding state in the figure indicates a state where the switch S1 is connected to the node Nb side.

In the polygonal line L43, the upward protrusion state in the drawing illustrates a state in which the switch S2 and the switch S3 are turned on, while the downward projection state illustrates a state in which the switch S2 and the switch S3 are turned off. Furthermore, in the polygonal line L49 and polygonal line L50, the upward protrusion state in the figure indicates the high level of each of the control signal CNTEN and the pulse signal CNTOUT, that is, the state of "1", while the downward protrusion state in the figure indicates the low level of each of the control signal CNTEN and pulse signal CNTOUT, that is, the state of "0".

In the example illustrated in FIG. 8, at time t41 before light emission of the LED 61, the connection destination of the switch S1 is set to the node Nb, and the switches S2 and S3 are set to be turned on. In addition, the control signal CNTEN is set to "0", and the current flowing through the constant current source I5 is set to 0 µA. At this time, the value of the pulse signal CNTOUT is "0".

In a state where the switch S2 and the switch S3 are turned on, when the voltage between the gate and the source of the transistor NM2 is VGS, the voltage V1 equals to (VDD−VGS) which is a difference between the power supply voltage VDD and the voltage VGS. This voltage (VDD−VGS) is input to the non-inverting input terminal of the comparator 122.

In addition to the voltage (VDD−VGS), a voltage corresponding to the offset of the comparator 122 is also generated in the voltage V3 of the inverting input terminal of the comparator 122, and the voltage difference from the voltage VDD is held at both ends of the capacitor C3. That is, while the value of the voltage V3 includes the offset of the comparator 122, the value is substantially (VDD−VGS).

Thereafter, at time t42, the LED driver 62 causes one LED 61, for example, the LED 61-1 to emit light. When the LED 61-1 emits light, the PD 63 receives reflected light from the human body, whereby a current Ipd is generated in the PD 63.

At time t43, the ADC unit 64 sets the connection destination of the switch S1 to the node Na, the integrating circuit 71 turns off the switch S2, and the pulse generating circuit 72 turns off the switch S3. This operation starts integration operation of the current Ipd to the capacitor C1.

This electrically connects the PD 63 and the capacitor C1 via the transistor NM1 and the switch S1, leading to accumulation of electric charges in the capacitor C1 in accordance with the generation of the current Ipd. Since the voltage applied to the gate of the transistor NM2 decreases in accordance with the increase in the accumulated electric charge in the capacitor C1, the voltage V1 also decreases (lowers) accordingly. In other words, the transistor NM2 generates a voltage difference V1 corresponding to the electric charge stored in the capacitor C1, that is, a voltage difference $\Delta V1$.

In addition, when the switch S3 is turned off, the comparator 122 compares the voltage V1 of the non-inverting input terminal with the voltage V3 of the inverting input terminal, and outputs a comparison result as the voltage V4 to the flip-flop 101. At this point, since the voltage V3 of the inverting input terminal is larger than the voltage V1 of the non-inverting input terminal, the voltage V4 is set to the low level, that is, "0". Therefore, in this state, the value of the pulse signal CNTOUT output from the flip-flop 101 is "0".

Thereafter, at time t44, the LED driver 62 stops the light emission of the LED 61, and the ADC unit 64 sets the connection destination of the switch S1 to the node Nb.

After the connection destination of the switch S1 is returned from the node Na to the node Nb in this manner, the integration operation is finished. At this time, the amount of change in the voltage V1 during the period of the integration operation is to be the voltage $\Delta V1$ proportional to the amount of reflected light received by the PD 63, that is, the total amount of reception of the reflected light.

For example, the length of the period from time t43 to time t44 during which the connection destination of the switch S1 is set to the node Na, that is, the length of the period during which the integration operation of the current Ipd is performed by the integrating circuit 71 is defined as integration time T0, the magnitude of the current Ipd is defined as Ipd and the capacitance value of the capacitor C1 is defined as C1. Under this setting, the voltage $\Delta V1$ is $\Delta V1 = T0 \times Ipd / C1$.

Note that while the above has described an example in which the integration operation of the current Ipd is started after the start of the light emission period of the LED 61 and the integration operation is finished together with the end of the light emission period of the LED 61, the period during which the integration operation of the current Ipd is performed can be any period as long as it is during the light emission period of the LED 61.

Since the value of the voltage V1 decreases by $\Delta V1$ by the integration operation of the current Ipd, the value of the voltage V1 becomes (VDD−VGS−$\Delta V1$) at the point of completion of the integration operation. This voltage V1= (VDD−VGS−$\Delta V1$) is to be supplied to the non-inverting input terminal of the comparator 122.

Thereafter at time t45, the ADC unit 64 sets the control signal CNTEN to "1" and together with this, the ramp waveform generating circuit 121 controls the constant current source I5 such that the current flowing through the constant current source I5 increases by a fixed amount at every predetermined unit time ts. In this example, control is performed to allow the current flowing through the constant current source I5 to increase by 1 µA at every unit time ts.

Here, the resistance value of the resistor R1 is defined as R1, and the capacitance value of the capacitor C2 is defined as C2. In this case, in a case where the time constant of R1×C2 is sufficiently larger than the unit time ts, the change in the voltage V2 as the output of the ramp waveform generating circuit 121 can be obtained as the waveform of slope similar to the gradient of the change in the current flowing through the constant current source I5. Since the inverting input terminal side of the comparator 122 is at high impedance, the same voltage waveform as the voltage V2 is obtained as the voltage V3 via the capacitor C3.

In this example, it is observed that the voltage V2 decreases with a constant gradient together with the increase in the current flowing through the constant current source I5 and that this results in a decrease of the voltage V3 similarly to the voltage V2. That is, it can be seen that a voltage signal (ramp wave) of a ramp waveform indicated by the voltage V3 is input to the inverting input terminal of the comparator 122.

The comparator 122 compares the ramp wave input to the inverting input terminal, that is, the voltage V3, with the voltage V1 reduced by $\Delta V1$ in accordance with the amount of reception of the reflected light input to the non-inverting input terminal, and outputs a comparison result as a pulse signal, more specifically, as the voltage V4 for obtaining the pulse signal.

In addition, the counter 65 starts counting the reference clock at time t45.

At this point, since the voltage V3=(VDD−VGS) of the inverting input terminal is larger than the voltage V1=(VDD VGS−$\Delta V1$) of the non-inverting input terminal, the voltage V4 being the output of the comparator 122 is the low level and the value of the pulse signal CNTOUT is also the low level, that is, remains at "0".

Thereafter, the voltage V3 gradually decreases. When the voltage V3 of the inverting input terminal becomes equal to the voltage V1 of the non-inverting input terminal at time t46, that is, after the voltage V3 decreases by $\Delta V1$, the voltage V4 being the output of the comparator 122 transitions to the high level. That is, the voltage V4 is inverted from "0" to "1".

This causes the flip-flop 101 to be reset, and the pulse signal CNTOUT output from the flip-flop 101 changes to the high level. That is, the value of the pulse signal CNTOUT is inverted from "0" to "1".

The counter 65 finishes counting of the reference clock at the timing when the value of the pulse signal CNTOUT becomes "1", and outputs the count result to the storage unit 66 as measurement data.

That is, the period T11 from the rising edge of the control signal CNTEN, which is the trigger signal for starting the AD conversion, to the rising edge of the pulse signal CNTOUT corresponds to the pulse width proportional to the voltage $\Delta V1$. The counter 65 measures the length of the period of the pulse width on the basis of the internal reference clock, so as to convert the pulse width of the pulse signal CNTOUT into a digital quantity and generate measurement data.

Furthermore, after the digital measurement data is obtained, the integrating circuit 71 turns on the switch S2 at time t47, and the pulse generating circuit 72 turns on the switch S3. In addition, at time t47, the control signal CNTEN is set to "0", leading to the value of the pulse signal CNTOUT being "0".

The period from time t44 to time t47 corresponds to the period T2 illustrated in FIG. 4, for example.

Measurement data for one LED 61 has been obtained by the operation so far, and thereafter, the operation for obtaining the measurement data of each of the LEDs 61 including the other LEDs 61 is performed continuously and repeatedly.

As described above, with the pulse wave sensor system 51 including an integral type AD conversion mechanism that integrates the current obtained by receiving the reflected light, converts it into voltage, and further converts the voltage into measurement data, it is possible to reduce the light emission time of the LED 61, leading to reduction of power consumption.

In particular, it is possible also in the present embodiment to achieve driving with the average current similar to the above-described first embodiment. Moreover, it is allowable to configure the second embodiment such that the selection of the light emission time, the drive current of the LED 61, the integration time T0, and the capacitor C1 can be controlled from the outside.

Note that embodiments of the present technology are not limited to the above-described embodiments but can be modified in a variety of ways within a scope of the present technology.

Furthermore, the present technology may be configured as follows.

(1)

A measurement circuit including:

a light receiving unit that receives light from an object;

an integrating unit that performs integration of a current generated in accordance with the reception of the light by the light receiving unit and generates a voltage according to the amount of reception of the light; and a pulse generating unit that generates a pulse signal having a pulse width corresponding to the amount of reception of the light on the basis of the voltage.

(2)

The measurement circuit according to (1) further including a light emitting unit that emits light toward the object, in which the light receiving unit receives the light emitted to the object by the light emitting unit and reflected by the object.

(3)

The measurement circuit according to (2), in which the integrating unit performs integration of the current in any period during a light emission period in which the light is emitted by the light emitting unit, and the pulse generating unit generates the pulse signal after the light emission period.

(4)

The measurement circuit according to any one of (1) to (3), further including a counter that generates digital measurement data corresponding to the amount of reception of the light by measuring the number of clocks input during the pulse width period of the pulse signal.

(5)

The measurement circuit according to any one of (1) to (4), in which the integrating unit integrates the current by accumulating electric charges in a capacitor in accordance with the generation of the current.

(6)

The measurement circuit according to (5), in which the integrating unit includes an amplifier on which the capacitor is connected between an inverting input terminal and an output terminal and that outputs the voltage corresponding to the electric charges accumulated in the capacitor.

(7)

The measurement circuit according to (5), in which the integrating unit includes a transistor in which the capacitor is connected to a gate and that generates the voltage corresponding to the electric charges accumulated in the capacitor.

(8)

The measurement circuit according to any one of (1) to (5), in which the pulse generating unit include:

a ramp waveform generating unit that generates a ramp wave having a voltage changing in a slope shape on the basis of the voltage obtained by the integrating unit; and a comparator that compares a predetermined voltage with the ramp wave and outputs a comparison result as the pulse signal.

(9)

The measurement circuit according to any one of (1) to (5), in which the pulse generating unit includes:

a ramp waveform generating unit that generates a ramp wave having a voltage changing in a slope shape; and a comparator that compares the voltage obtained by the integrating unit with the ramp wave and outputs a comparison result as the pulse signal.

(10)

A driving method for driving a measurement circuit including:

a light receiving unit that receives light from an object;

an integrating unit that integrates a current generated in accordance with the reception of the light by the light receiving unit and that generates a voltage in accordance with the amount of reception of the light; and a pulse generating unit that generates a pulse signal having a pulse width corresponding to the amount of reception of the light on the basis of the voltage, the driving method including generating the voltage by the integrating unit and generating the pulse signal by the pulse generating unit.

(11)

An electronic instrument including:

a light receiving unit that receives light from an object;

an integrating unit that performs integration of a current generated in accordance with the reception of the light by the light receiving unit and generates a voltage according to the amount of reception of the light; and a pulse generating unit that generates a pulse signal having a pulse width corresponding to the amount of reception of the light on the basis of the voltage.

REFERENCE SIGNS LIST

51 Pulse wave sensor system
61-1 to 61-3, 61 LED
62 LED Driver
63 PD
64 ADC unit
65 Counter
71 Integrating circuit
72 Pulse generating circuit
101 Flip-flop
111 Amplifier
121 Ramp waveform generating circuit
122 Comparator

The invention claimed is:

1. A measurement circuit, comprising:
 circuitry configured to:
  control a first light emitting diode (LED) to start emission of first light at a start of a first light emission period, wherein the first light is emitted towards an object;
  receive the first light reflected by the object;
  generate a first current based on the received first light;
  execute integration of the generated first current in the first light emission period, wherein the integration of the generated first current is completed before an end of the first light emission period;
  control the first LED to stop the emission of the first light at the end of the first light emission period;
  generate a first voltage based on the integration of the generated first current;
  generate a first pulse signal having a pulse width based on the generated first voltage;
  control a second light emitting diode (LED) to start emission of second light at a start of a second light emission period, wherein
   the second light is emitted towards the object, and
   the second light emission period is different from the first light emission period;
  receive the second light reflected by the object;
  generate a second current based on the received second light;
  execute integration of the generated second current in the second light emission period, wherein the integration of the generated second current is completed before an end of the second light emission period;
  control the second LED to stop the emission of the second light at the end of the second light emission period;
  generate a second voltage based on the integration of the generated second current;
  generate a second pulse signal having a pulse width based on the generated second voltage;
  control a counter to:
   measure a first number of clocks in a first pulse width period of the first pulse signal, wherein
    the counter is stopped during the first light emission period, and
    the measurement of the first number of clocks is executed after the end of the first light emission period and before a start of the second light emission period; and
   measure a second number of clocks in a second pulse width period of the second pulse signal, wherein
    the counter is stopped during the second light emission period, and
    the measurement of the second number of clocks is executed after the end of the second light emission period; and
  generate digital measurement data based on the measured first number of clocks and the measured second number of clocks.

2. The measurement circuit according to claim 1, wherein the circuitry is further configured to generate the first pulse signal after the end of the first light emission period.

3. The measurement circuit according to claim 1, further comprising a capacitor configured to accumulate electric charges based on the generated first current, wherein
 the circuitry is further configured to execute the integration of the generated first current based on the accumulated electric charges in the capacitor.

4. The measurement circuit according to claim 3, further comprising an amplifier, wherein
 the capacitor is connected between an inverting input terminal of the amplifier and an output terminal of the amplifier, and
 the output terminal is configured to output the first voltage based on the electric charges accumulated in the capacitor.

5. The measurement circuit according to claim 3, further comprising a transistor, wherein
 the capacitor is connected to a gate of the transistor, and
 the gate of the transistor is configured to generate the first voltage based on the electric charges accumulated in the capacitor.

6. The measurement circuit according to claim 1, wherein the circuitry is further configured to:
 generate a ramp wave having a third voltage that changes in a slope shape, wherein the ramp wave is generated based on the first voltage;
 compare a fourth voltage with the ramp wave; and
 output a comparison result as the first pulse signal based on the comparison of the fourth voltage with the ramp wave.

7. The measurement circuit according to claim 1, wherein the circuitry is further configured to:
 generate a ramp wave having a third voltage that changes in a slope shape;
 compare the first voltage with the ramp wave; and
 output a comparison result as the first pulse signal based on the comparison of the first voltage with the ramp wave.

8. A driving method, comprising:
 controlling a first light emitting diode (LED) to start emission of first light at a start of a first light emission period, wherein the first light is emitted towards an object;
 receiving the first light reflected by the object;
 generating a first current based on the received first light;
 executing integration of the generated first current in the first light emission period, wherein the integration of the generated first current is completed before an end of the first light emission period;
 controlling the first LED to stop the emission of the first light at the end of the first light emission period;
 generating a first voltage based on the integration of the generated first current;
 generating a first pulse signal having a pulse width based on the generated first voltage;
 controlling a second light emitting diode (LED) to start emission of second light at a start of a second light emission period, wherein
  the second light is emitted towards the object, and
  the second light emission period is different from the first light emission period;
 receiving the second light reflected by the object;
 generating a second current based on the received second light;
 executing integration of the generated second current in the second light emission period, wherein the integration of the generated second current is completed before an end of the second light emission period;
 controlling the second LED to stop the emission of the second light at the end of the second light emission period;
 generating a second voltage based on the integration of the generated second current;

generating a second pulse signal having a pulse width based on the generated second voltage;

measuring a first number of clocks in a first pulse width period of the first pulse signal, wherein
the measurement is stopped during the first light emission period, and
the measurement of the first number of clocks is executed after the end of the first light emission period and before a start of the second light emission period;

measuring a second number of clocks in a second pulse width period of the second pulse signal, wherein
the measurement is stopped during the second light emission period, and
the measurement of the second number of clocks is executed after the end of the second light emission period; and generating digital measurement data based on the measured first number of clocks and the second number of clocks.

9. An electronic instrument, comprising:
a first light emitting diode (LED);
a second LED;
a counter; and
circuitry configured to:
control the first LED to start emission of first light at a start of a first light emission period, wherein the first light is emitted towards an object;
receive the first light reflected by the object;
generate a first current based on the received first light;
execute integration of the generated first current in the first light emission period, wherein the integration of the generated first current is completed before an end of the first light emission period;
control the first LED to stop the emission of the first light at the end of the first light emission period;
generate a first voltage based on the integration of the generated first current;
generate a first pulse signal having a pulse width based on the generated first voltage;
control a second light emitting diode (LED) to start emission of second light at a start of a second light emission period, wherein
the second light is emitted towards the object, and
the second light emission period is different from the first light emission period;
receive the second light reflected by the object;
generate a second current based on the received second light;
execute integration of the generated second current in the second light emission period, wherein the integration of the generated second current is completed before an end of the second light emission period;
control the second LED to stop the emission of the second light at the end of the second light emission period;
generate a second voltage based on the integration of the generated second current;
generate a second pulse signal having a pulse width based on the generated second voltage;
control a counter to:
measure a first number of clocks in a first pulse width period of the first pulse signal, wherein
the counter is stopped during the first light emission period, and
the measurement of the first number of clocks is executed after the end of the first light emission period and before a start of the second light emission period; and
measure a second number of clocks in a second pulse width period of the second pulse signal, wherein
the counter is stopped during the second light emission period, and
the measurement of the second number of clocks is executed after the end of the second light emission period; and
generate digital measurement data based on the measured first number of clocks and the second number of clocks.

10. The measurement circuit according to claim 1, wherein the circuitry is further configured to:
control a third light emitting diode (LED) to start emission of third light at a start of a third light emission period, wherein the third light is emitted towards the object;
receive the third light reflected by the object;
generate a third current based on the received third light;
execute integration of the generated third current in the third light emission period, wherein the integration of the generated third current is completed before an end of the third light emission period;
control the third LED to stop the emission of the third light at the end of the third light emission period;
generate a third voltage based on the integration of the generated third current; and
generate a third pulse signal having a pulse width based on the generated third voltage;
control the counter to measure a third number of clocks in a third pulse width period of the third pulse signal, wherein
the counter is stopped during the third light emission period, and
the measurement of the third number of clocks is executed after the end of the third light emission period; and
generate the digital measurement data based on the measured first number of clocks, the measured second number of clocks, and the measured third number of clocks.

* * * * *